US009895438B2

(12) United States Patent
Dalgleish et al.

(10) Patent No.: US 9,895,438 B2
(45) Date of Patent: Feb. 20, 2018

(54) TREATMENT OF CANCER WITH NALTREXONE

(71) Applicant: Cancer Vaccine Institute, London (GB)

(72) Inventors: Angus Dalgleish, London (GB); Rachel Allen, London (GB)

(73) Assignee: Cancer Vaccine Institute (GB)

( * ) Notice: Subject to any disclaimer, the term of this patent is extended or adjusted under 35 U.S.C. 154(b) by 0 days.

(21) Appl. No.: 14/890,300

(22) PCT Filed: May 12, 2014

(86) PCT No.: PCT/GB2014/051439
§ 371 (c)(1),
(2) Date: Nov. 10, 2015

(87) PCT Pub. No.: WO2014/181131
PCT Pub. Date: Nov. 13, 2014

(65) Prior Publication Data
US 2016/0106832 A1    Apr. 21, 2016

(30) Foreign Application Priority Data

May 10, 2013 (GB) .................................. 1308440.5

(51) Int. Cl.
A61K 31/485     (2006.01)
A61K 39/39      (2006.01)
A61K 45/06      (2006.01)
A61K 31/593     (2006.01)
A61K 39/04      (2006.01)
C07D 489/08     (2006.01)
A61K 39/00      (2006.01)

(52) U.S. Cl.
CPC ............ A61K 39/39 (2013.01); A61K 31/485 (2013.01); A61K 31/593 (2013.01); A61K 39/04 (2013.01); A61K 45/06 (2013.01); C07D 489/08 (2013.01); A61K 2039/55511 (2013.01); A61K 2039/585 (2013.01)

(58) Field of Classification Search
CPC .................................................. A61K 31/485
See application file for complete search history.

(56) References Cited

U.S. PATENT DOCUMENTS 6,136,780 A * 10/2000 Zagon .................. A61K 31/485
                                                 514/18.5
6,288,074 B1    9/2001 Bihari
6,384,044 B1    5/2002 Bihari
2009/0169508 A1 7/2009 Wu et al.
2011/0136845 A1 6/2011 Trawick et al.

FOREIGN PATENT DOCUMENTS

WO    2006117573 A1    11/2006

OTHER PUBLICATIONS

Gonzalez-Reyes et al. Cancer Immunol. Immunother., 2011, vol. 60, pp. 217-226.*
Sato et al. Cancer Microenvironment, 2009, vol. 2 (Suppl. 1), pp. S205-S214.*
Nilsson et al. Journal of Clinical Oncology, 2004, vol. 22, suppl. 14, p. 4705 (Abstract Attached).*
Straus et al. Blood, 2011, vol. 117, No. 20, pp. 5314-5320.*
Tappeh Khosrow Hazrati et al: "A Novel Adjuvant, Mixture of Alum and Naltrexone, Elicits Humoral Immune Responses for Excreted/Secreted Antigens of Toxoplasma gondii Tachyzoites Vaccine in Balb/c Murine Model" Turkiye Parazitoloji Dergisi, vol. 37, No. 2, Jun. 2013 (Jun. 2013). pp. 92-96, XP002725932, ISSN: 1300-6320 abstract p. 96, left-hand column, last paragraph.
International Search Report for Application No. PCT/GB2014/051439 dated Jul. 2, 2014.
Jamali et al., "A novel adjuvant, the general opioid antagonist naloxone, elicits a robust cellular immune response for a DNA vaccine", International Immunology, Jan. 27, 2009, vol. 21, No. 3, pp. 217-225.

* cited by examiner

Primary Examiner — James D. Anderson
(74) Attorney, Agent, or Firm — Lerner, David, Littenberg, Krumholz & Mentlik, LLP

(57) ABSTRACT

The present invention provides novel therapeutic applications of low dose naltrexone (LDN). Said applications have been determined in light of the discovery by the present inventors that naltrexone acts as an antagonist of Toll-like receptor 9 (TLR9), an innate immune receptor which elicits the production of inflammatory cytokines when agonized. Chronic inflammation and TLR9 overexpression are characteristics of a number of disorders, including certain cancers. Accordingly, the present invention provides novel uses of naltrexone in the treatment of a subject having a disorder characterized by TLR9 overexpression and/or overactivity of TLR9-mediated signalling. The present invention also provides novel uses of naltrexone in the supportive care of subject having a tumor/cancer, and methods of treating and providing supportive care to a subject, comprising the administration of naltrexone.

4 Claims, 2 Drawing Sheets

TREATMENT OF CANCER WITH NALTREXONE

CROSS REFERENCE TO RELATED APPLICATIONS

The present application is a national phase entry under 35 U.S.C. § 371 of International Application No. PCT/GB2014/051439 filed May 12, 2014, published as WO 2014/181131, which claims priority from Great Britain Patent Application No. 1308440.5, filed May 10, 2013, the disclosures of which are hereby incorporated herein by reference.

FIELD OF THE INVENTION

This invention relates to the treatment and supportive care of a subject having a disorder characterised by aberrant activity of the innate immune system, notably certain forms of cancer.

BACKGROUND OF THE INVENTION

Naltrexone is an orally-administered opioid antagonist with the chemical name morphinan-6-one,17-(cyclopropylmethyl)-4,5-epoxy-3,14-dihydroxy-(5α).

The molecular formula of naltrexone is $C_{20}H_{23}NO_4$ and its molecular weight is 341.41 in the anhydrous form (<1% maximum water content). The chemical structure of naltrexone is shown below.

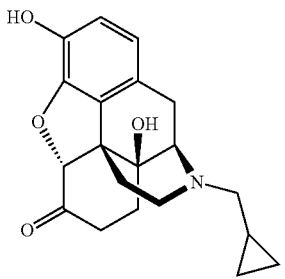

Naltrexone is commonly used as a treatment for opiate addiction. A number of patients, however, use low doses of naltrexone (LDN) as an off-label treatment for a range of immune-related pathologies and cancer. There is preliminary evidence that LDN may be effective in Multiple Sclerosis (Rahn et al. 2011), Crohn's disease (Smith et al. 2011) and certain cancers.

With regard to cancer, Zagon and McLaughlin (1983) and Hytrek et al. (1996) reported LDN-mediated inhibition of murine neuroblastoma and human colon cancer cell growth respectively, when evaluated in murine xenograft models. Furthermore, combinations of LDN with additional therapeutic agents have been found to be effective against the growth and progression of certain cancer types, for example Donahue et al. (2011a) reported potent anti-proliferative effects of LDN and cisplatin on human ovarian cancer cells both in vitro and in an in vivo murine xenograft model. In the clinic, Berkson et al. (2006) described the long term survival of a patient having pancreatic cancer with metastasis to liver, following treatment with α-lipoic acid in combination with LDN; the authors have since reported similar observations in three further patients with metastatic pancreatic cancer (Berkson et al. 2009).

The role of LDN in the above observations has so far largely been explained by reference to the antagonistic action of LDN on the opioid growth factor receptor (OGFr). OGFr recognises opioid growth factor (OGF, also referred to as [$Met^5$]-enkephalin), and intermittent doses of naltrexone appear to provide a temporary blockade that triggers upregulation of the receptor (Hytrek et al. 1996). This upregulation of OGFr has been found to result in decreased in vitro proliferation of cells representative of pancreatic, colorectal and squamous cell carcinomas (Donaghue et al. 2011 b).

However, a potential mechanism for LDN as a direct immunomodulator has been revealed in studies by Hutchinson et al. (2008), who demonstrated that in addition to its effects on OGFr, naltrexone can weakly antagonise TLR4, a member of the Toll-like receptor (TLR) family. Pattern recognition receptors such as TLRs allow immune cells to detect the presence of pathogens or self-derived danger signals, and instruct them to trigger an immune response. Innate immune activation is a necessary step for eliciting subsequent adaptive immune responses, and given the powerful inflammatory potential of TLRs, their activity must be tightly controlled. In general, TLR stimulation elicits the induction of feedback mechanisms, but when this fails, TLR overactivity can lead to inappropriate immune responses, immune exhaustion and/or autoimmunity.

SUMMARY OF THE INVENTION

The present inventors have found that naltrexone also acts as an antagonist of the innate immune receptor TLR9. This observation has profound implications for the use of LDN as an immunomodulator, and has enabled the present inventors to determine a number of novel therapeutic applications, notably in the field of cancer therapy and supportive care.

According to a first aspect, the present invention provides a pharmaceutical composition comprising naltrexone, for use in the treatment of a subject having a disorder which is characterised by TLR9 overexpression and/or overactivity of TLR9-mediated signalling.

According to a second aspect, the present invention provides a pharmaceutical composition comprising naltrexone, for use in the supportive care of a subject having a tumour/cancer.

According to a third aspect, the present invention provides a method of treating a subject having a disorder which is characterised by TLR9 overexpression and/or overactivity of TLR9-mediated signalling; wherein the method comprises administering to the subject, a pharmaceutical composition comprising naltrexone.

According to a fourth aspect, the present invention provides a method of providing supportive care to a subject having a tumour/cancer, comprising administering to the subject, a pharmaceutical composition comprising naltrexone.

BRIEF DESCRIPTION OF THE FIGURES

The invention is described with reference to the accompanying figures, wherein.

DETAILED DESCRIPTION OF THE INVENTION

The discovery by the present inventors that naltrexone acts as an antagonist of TLR9 has enabled the determination of novel therapeutic applications of LDN, notably in the field of cancer therapy and supportive care.

Figure 1:
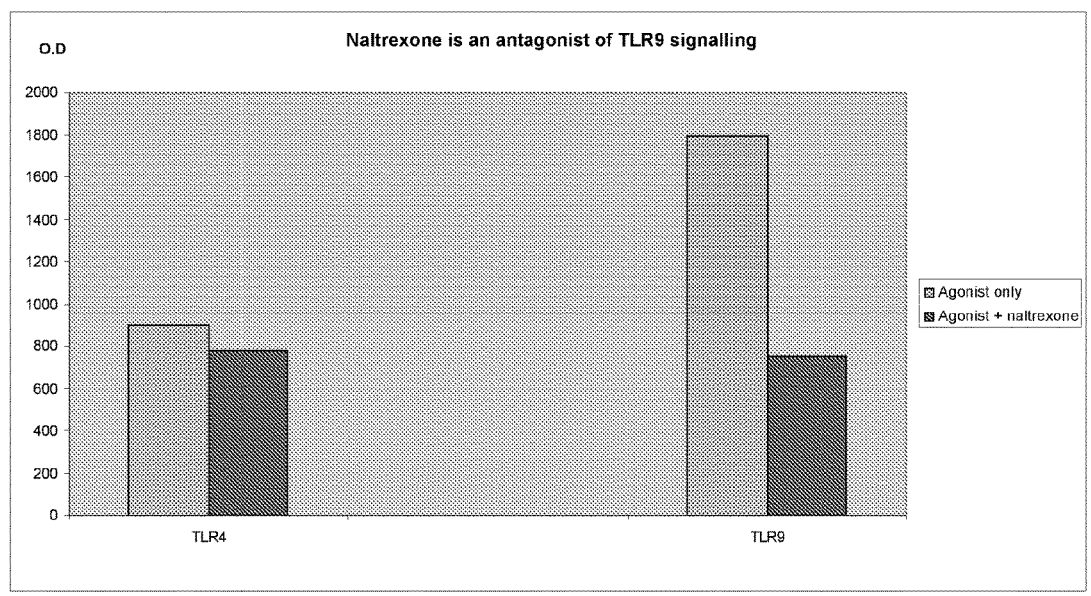
FIG. 1 shows antagonism of TLR9 by naltrexone. Samples and controls were tested in duplicate on recombinant HEK-293 cell lines expressing the various TLR and NOD receptors with an alkaline phosphatase reporter gene. Cells were incubated with or without 1 µM naltrexone in an antagonist assay using the Invivogen panel of TLR and NOD signalling transfectants. Results shown are for TLR4 and TLR9, TLR activation results are given as optical density (O.D.) values, which have been confirmed in three independent experiments.
Figure 2:
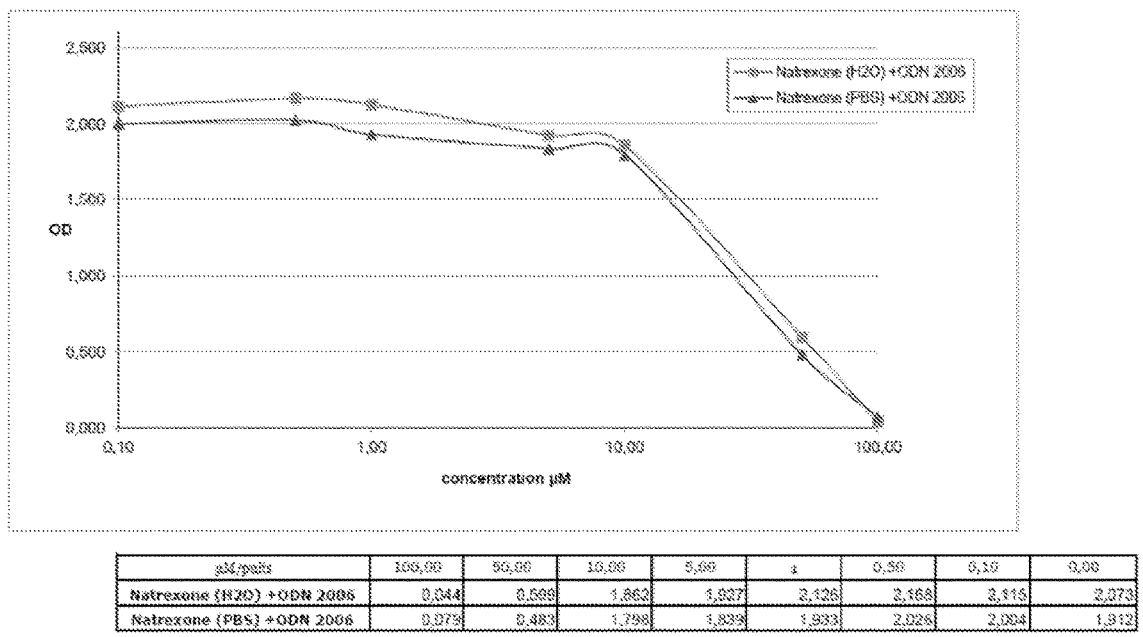
FIG. 2 shows the ability of naltrexone diluted in phosphate buffered saline (PBS) or $H_2O$ to inhibit TLR9 at various concentrations, for a TLR9-transfected cell line (as described above).

Certain pattern recognition receptors, such as TLR4, are located on the cell surface, whilst others such as TLR7, TLR8 and TLR9 are found within the cell. As naltrexone can enter cells by passive diffusion (Cheng et al. 2009), the present inventors sought to determine whether it might antagonise any intracellular TLR in addition to the cell-surface protein TLR4. A striking antagonistic effect was observed for TLR9, for which LDN inhibited recognition of CpG DNA (FIG. 1), and a subsequent titration suggested an IC50 of approximately 50 µM (FIG. 2). Furthermore, the mild antagonistic effect on TLR4 observed by Hutchinson et al. (2008) was replicated.

TLR9 is an innate immune receptor which, upon detection of unmethylated CpG DNA, elicits the production of type 1 interferons and other inflammatory cytokines (TNFα, IL-2, IL-6). The nature of the response generated following TLR9 activity can vary according to the intracellular location where the receptor interacts with its ligands, whether CD14 acts as a co-receptor, the CpG sequence of the DNA ligand, and the cell type involved (Weber et al. 2012). The form of administration (local vs systemic) of CpG DNA can also determine whether the final outcome of TLR9 signalling is inflammatory or inhibitory (Wingender et al. 2006).

TLR9 is expressed in macrophages, B cells and dendritic cells, and the plasmacytoid dendritic cell (pDC) subset in particular. pDC are specialised for the rapid production of the inflammatory cytokines known as Type I interferons (IFN-I) following infection and act as central regulators of inflammation and T cell responses as well as modulating other innate immune cell functions (Takagi et al. 2011). The type 1 interferons produced by pDC allow killing of intracellular infections and have potent effects on other immune cells, mediating DC maturation, monocyte and natural killer cell activation, enhancement of the adaptive immune response and ability to respond to other TLR stimuli. Thus, the immunomodulatory functions of low dose naltrexone mediated through antagonism of TLR9 would primarily affect pDC function, although downstream effects following pDC modulation would be exerted on a wide range of cells.

The natural role of TLR9 is to stimulate an immune response. It may seem counter-intuitive that TLR9 antagonism would be an effective therapy or supportive care for a subject diagnosed with cancer, given that an effective anti-tumour immune response, or agonism of the immune system, would be beneficial. However, TLR9 overactivity can have detrimental effects on the immune response; pDC activity is beneficial at the initiation of an immune response, but chronic activation of TLR9 can inhibit T and B cell responses. Sustained TLR9 activation leads to immunosuppression via indoleamine 2,3-dioxygenase (IDO), Programmed cell death ligand 1 (PDL1) and TNF-related apoptosis-inducing ligand (TRAIL) (Boasso et al. 2011). In this instance IDO, which is produced by pDC in response to TLR7/9 signalling, exerts inhibitory effects, which are proposed to result in immunosuppression, and a lack of effective T cell responses. TLR9 can also be tolerogenic to B cells in the presence of apoptotic cells.

Although specialised for detection of microbial nucleic acids, TLR9 can recognise, and be overstimulated by self-nucleic acids in certain pathological conditions. In systemic lupus erythematosus (SLE), self-DNA immune complexes captured within neutrophil extracellular traps can subsequently be recognised by TLR9 within pDC to trigger Type I IFN production; a similar situation can occur in psoriasis.

If TLR9 overactivity can result in immune dysregulation, it is therefore logical that its antagonism by LDN would dampen down chronic inflammatory responses, in order to allow directed and beneficial immune responses to (re) emerge. Cancer, for example, is associated with inflammation and it has been suggested that about 25% of cancers are linked to chronic inflammation (Mantovani 2011). Thus LDN treatment can reduce inflammation to enable the generation of effective anti-tumour adaptive immune responses, notably in cancers where inflammation is driven by TLR9 overexpression in the cancer or microenvironment.

LDN-mediated inhibition of TLR9 could also allow beneficial immune responses to be triggered via other members of the TLR family; this would be of particular use in providing supportive care to a patient suffering from any type of cancer. Approximately 89% of cases of cancer in the UK are diagnosed in people over 50 (Cancer Research UK), therefore the combination of cancer and age-related immune depression (immunosenescence) in a patient can result in substantial imbalance to the immune system. Modulation of a subset of receptors such as TLR4 and TLR9 via naltrexone whilst allowing other members of the TLR family to be stimulated, or stimulating the immune system via another pathway, could provide a simple inhibition of excess immune activity or allow a more subtle skewing of immune responses. Aside from treatment, this could provide improvements in quality of life to those suffering from cancer and thus could be an effective strategy for supportive care.

As used herein "naltrexone" refers to morphinan-6-one, 17-(cyclopropylmethyl)-4,5-epoxy-3,14-dihydroxy-(5α) having the above chemical structure, and pharmaceutically acceptable salts, solvates, hydrates, stereoisomers, clathrates and prodrugs thereof. The use of naloxone, a structural analogue of naltrexone which the skilled person would expect to also act as an antagonist of TLR9, is within the purview of the invention and is encompassed within the term "analogue" used in the description and the claims. Similarly, methylnaltrexone is also envisaged as a suitable analogue for use in all aspects of the invention. The preferred form of naltrexone is as its hydrochloride salt form.

As used herein, the terms "agonist" and "antagonist" have their conventional meanings as used in the art.

As used herein, the term "overexpression of TLR9" refers to the level of TLR9 mRNA and/or protein expressed in cells of a given tissue being elevated in comparison to the levels of TLR9 as measured in normal cells (free from disease) of the same type of tissue, under analogous conditions. Said TLR9 mRNA and/or protein expression level may be determined by a number of techniques known in the art including, but not limited to, quantitative RT-PCR, western blotting, immunohistochemistry, and suitable derivatives of the above.

As used herein, the term "overactivity of TLR9-mediated signalling" refers to the level of TLR9-mediated signalling activity, including the activity of downstream effectors thereof, being elevated in comparison to the level of such activity as measured in the same tissue type (free from disease), under analogous conditions. Said elevated activity of downstream effectors of TLR9-mediated signalling may not necessarily be caused by increased expression and/or activity of TLR9; a downstream effector in an immune cascade/pathway mediated by inter alia, TLR9 may exhibit overactivity due to aberrant activity of another upstream component of the cascade/pathway; however if the activity of said downstream effector is mediated (at least in part) by TLR9, then antagonism of TLR9 may alter activity of said downstream effector for therapeutic effect. Accordingly, disorders exhibiting overactivity of downstream effectors as described above may also be considered as being characterised by overactivity of TLR9-mediated signalling. Downstream effectors of TLR9-mediated signalling include, but are not limited to; cells, notably those associated with the immune system such as B cells and dendritic cells (for example plasmacytoid dendritic cells) (said cells may themselves express TLR9), wherein the activity of said cells may be mediated by inter alia, TLR9; and peptides/proteins, notably those associated with an immune response such as cytokines (for example TNFα, IL-2, IL-6) and interferons (for example IFN-I), wherein the expression, secretion and/or activity of said proteins may be mediated by inter alia, TLR9. Downstream effectors of TLR9-mediated signalling may be present in a different tissue to the TLR9 proteins which mediate their activity. Techniques known in the art which may be used to determine the level of TLR9-mediated signalling activity include, but are not limited to; cell-based assays comprising analysis of transcription and/or translation of a target gene and/or protein of TLR9-mediated signalling; cell-based assays comprising analysis of cell phenotype and activity; cell-based assays comprising analysis of phosphorylation, proteolytic processing and/or otherwise modification of at least one downstream component of TLR9-mediated signalling; nucleic acid sequence analysis of TLR9 genes and/or RNA transcripts. Generally, but not necessarily, overexpression of TLR9 will result in overactivity of TLR9-mediated signalling. Overactivity of TLR9-mediated signalling may not necessarily be the result of overexpression of TLR9, for example in instances where the TLR9 gene and/or protein comprises activating mutations.

As used herein, the terms "treating" and "treatment" and "to treat" refer to both 1) therapeutic measures that cure, slow down, and/or halt progression of a diagnosed pathologic condition or disorder and 2) prophylactic or preventative measures that prevent and/or slow the development of a targeted pathologic condition or disorder. Thus, those in need of treatment include those already with the disorder; those prone to have the disorder; and those in whom the disorder is to be prevented. In some instances, a subject is successfully "treated" for cancer according to the novel applications of the present invention if the patient shows one or more of the following: a reduction in the number of, or complete absence of, cancer cells; a reduction in the tumour size; inhibition of, or an absence of, cancer cell infiltration into peripheral organs including, for example, the spread of cancer into soft tissue and bone; inhibition of, or an absence of, tumour metastasis; inhibition of, or an absence of, tumour growth; reduced morbidity and mortality; reduction in tumourigenicity, tumourigenic frequency, or tumourigenic capacity of a tumour; reduction in the number or frequency of cancer stem cells in a tumour; differentiation of tumourigenic cells to a non-tumourigenic state; or some combination of effects.

As used herein "supportive care", in the context of the treatment of a tumour/cancer, refers to that which helps the patient to cope with cancer and the treatment of it—from pre-diagnosis, through the process of diagnosis and treatment, to cure, continuing illness or death. Supportive care includes, but is not limited to, symptom control, complementary therapies, management of the side-effects of treatment, psychological support, rehabilitation, self help and support, palliative care, end-of-life care. Accordingly, supportive care is not given with the expectation of treating the tumour/cancer in question (in accordance with the above definition), but improving quality of life for the patient, for example through symptom relief.

As used herein, the terms "cancer" and "cancerous" refer to or describe the physiological condition in mammals in which a population of cells are characterized by unregulated cell growth, proliferation and/or survival. Examples of cancer include, but are not limited to, carcinoma, lymphoma, blastoma, sarcoma, myeloma and leukaemia.

As used herein, the terms "tumour" or "neoplasm" refers to any mass of tissue that results from excessive cell growth, proliferation and/or survival, either benign (noncancerous) or malignant (cancerous), including pre-cancerous lesions.

As used herein, the term "tumourigenic" refers to the functional features of a solid tumour stem cell including the properties of self-renewal (giving rise to additional tumourigenic cancer stem cells) and proliferation to generate all other tumour cells (giving rise to differentiated and thus non-tumourigenic tumour cells) that allow solid tumour stem cells to form a tumour. These properties of self-renewal and proliferation to generate all other tumour cells confer on cancer stem cells the ability to form palpable tumours upon serial transplantation into an immunocompromised host (e.g., a mouse) compared to non-tumourigenic tumour cells, which are unable to form tumours upon serial transplantation. It has been observed that non-tumourigenic tumour cells may form a tumour upon primary transplantation into an immunocompromised host after obtaining the tumour cells from a solid tumour, but those non-tumourigenic tumour cells do not give rise to a tumour upon serial transplantation.

As used herein, the term "tumour/cancer microenvironment" refers to non-malignant cells, including extracellular features thereof, which support the malignant cells of a tumour/cancer in their growth, survival and/or metastasis. The non-malignant cells, also called stromal cells, may occupy or accumulate in the same cellular space as malignant cells, or the cellular space adjacent or proximal to malignant cells, which modulate tumour cell growth or survival. Non-malignant cells of the tumour microenvironment include, but are not limited to, fibroblasts, myofibroblasts, glial cells, epithelial cells, adipocytes, vascular cells (including blood and lymphatic vascular endothelial cells and pericytes), resident and/or recruited inflammatory and immune (e.g., macrophages, dendritic cells, myeloid suppressor cells, granulocytes, lymphocytes, etc.), resident and/or recruited stem cells that are capable of giving rise to or differentiating into any of the above-noted non-malignant cells, and any functionally distinct subtypes of the above-noted cells as known in the art.

As used herein, the term "subject" refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

As used herein, the term "immunomodulator" refers an agent whose action on the immune system leads to an immediate or delayed enhancement or reduction of the activity of at least one pathway involved in an immune response. Said response may be naturally occurring or artificially triggered; as part of the innate or adaptive immune system; or both.

In one embodiment, the pharmaceutical compositions of the present invention are used to modulate an immune response so as to treat a subject having a disorder characterised by TLR9 overexpression and/or overactivity of TLR9-mediated signalling. The above features would be known to the skilled person as characteristics of the disorder to be treated. Disorders characterised by TLR9 overexpression and/or overactivity of TLR9-mediated signalling include, but are not limited to Crohn's disease, systemic lupus erythematosus, psoriasis, certain cancers. The subject to be treated may themselves be characterised as having TLR9 overexpression and/or overactivity of TLR9-mediated signalling. A subject may be characterised as such by way of a diagnostic test to determine the level of TLR9 expression and/or TLR9-mediated signalling (notably in cells pathologically associated with said disorder), relative to the levels in the same tissue type (when free from disease) under analogous conditions. Techniques known in the art which may be used to determine the level of TLR9 expression and/or TLR9-mediated signalling include, but are not limited to, those stated above. Preferably, said disorder is a tumour/cancer. More preferably, the tumour/cancer and/or the microenvironment thereof is characterised as comprising TLR9 overexpression and/or overactivity of TLR9-mediated signalling; such tumours/cancers include, but are not limited to, those selected from the group consisting of breast cancer, cervical squamous cell carcinoma, gastric carcinoma, glioma, hepatocellular carcinoma, lung cancer, melanoma, prostate cancer, recurrent glioblastoma, recurrent non-Hodgkin lymphoma, colorectal cancer. However, the pharmaceutical compositions of the invention being used in the treatment of subjects having other tumours/cancers, with the above characteristics (the tumour/cancer and/or the microenvironment thereof being characterised as comprising TLR9 overexpression and/or overactivity of TLR9-mediated signalling) is also envisaged. The subject may also be administered, or has been administered, at least one chemotherapeutic agent in addition to naltrexone, preferably wherein the agent and dose thereof is selected so as to reduce immune suppression; such agents include, but are not limited to, Revlimid (preferably administered at a dose between 5 mg and 25 mg), Cyclophosphamide (preferably administered at a dose between 50 mg and 100 mg), Gemcitabine (preferably administered at an administered dose between 250 mg/kg and 2000 mg) or carboplatin at a dose of 4-6 Areas Under the Curve (AUC).

In another embodiment, the present invention provides a method of treating a subject having a disorder characterised by TLR9 overexpression and/or overactivity of TLR9-mediated signalling; wherein the method comprises administering to the subject, a pharmaceutical composition of the invention. Said method of treatment has the same optional and preferred features as the use of the pharmaceutical composition recited in the preceding paragraph.

In another embodiment, the pharmaceutical compositions of the present invention, optionally when administered with, prior to, or after at least one other immunomodulator, are used to modulate an immune response in order to provide supportive care to a subject having a tumour/cancer. Said tumours/cancers are not limited to those comprising TLR9 overexpression and/or overactivity of TLR9-mediated signalling. Accordingly, examples include, but are not limited to carcinoma, lymphoma, blastoma, sarcoma, and leukaemia; more particular examples of such tumours/cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, melanoma, vulval cancer, thyroid cancer, hepatic carcinoma and various types of head and neck cancers. If used, the immunomodulator is preferably an immune agonist, i.e. an agent which elicits and/or augments an immune response, for example a vaccine. More preferably, the immune agonist is selected from the group consisting of cyclophosphamide; Revlimid; Imiquimod; a whole cell Mycobacteria, preferably a rough strain of *Mycobacterium vaccae* or *Mycobacterium obuense* (as described in WO 07/071978); Daunorubicin; Oxaliplatin; 5-Fluorouracil; Gemcitabine; Zometa. The subject to be given supportive care may themselves be characterised as having TLR9 overexpression and/or overactivity of TLR9-mediated signalling. A subject may be characterised as such by way of a diagnostic test to determine the level of TLR9 expression and/or TLR9-mediated signalling, relative to the levels in the same tissue type (when free from disease) under analogous conditions. Techniques known in the art which may be used to determine the level of TLR9 expression and/or TLR9-mediated signalling include, but are not limited to, those stated above. Wherein the subject is characterised as such; preferably the cells of the immune system in which TLR9 is natively expressed are characterised as having overexpression of TLR9. Such cells include, but are not limited to macrophages; B cells; and dendritic cells, notably plasmacytoid dendritic cells. Also wherein the subject is characterised as such; the tumour/cancer, and or the microenvironment thereof, may be identified as having TLR9 overexpression and/or overactivity of TLR9-mediated signalling.

In another embodiment, the present invention provides a method of providing supportive care to a subject having a tumour cancer. Said method of providing supportive care has the same optional and preferred features as the use of the pharmaceutical composition recited in the preceding paragraph.

According to the embodiments outlined above, naltrexone, as part of the pharmaceutical composition, is preferably administered to a subject at a dose between 0.01 mg/kg and 0.08 mg/kg, more preferably between 0.03 mg/kg and 0.06 mg/kg, most preferably between 0.04 mg/kg and 0.05 mg/kg. The composition can be administered in any conventional way. Administration can be by oral or parenteral administration, preferably oral administration. However, other routes of administration are also envisaged.

It has also been realised that naltrexone preferably low dose naltrexone (including its pharmaceutically acceptable salts, solvates, hydrates, stereoisomers, clathrates, prodrugs and analogues thereof) are suitable for use as a vaccine adjuvant. The naltrexone may be administered simultaneously, separately or sequentially with an immunogen. For examples the naltrexone may be administered either before or after administration of the immunogen (vaccine). In this aspect, the naltrexone is believed to stimulate cytotoxic T cells activation via the stimulation of dendritic cells. Accordingly, naltrexone can therefore be used in this context to help promote an immune response against various disorders, including cancer, e.g. metastatic melanoma.

There is therefore envisaged vaccine compositions comprising naltrexone and an immunogen.

The invention is now illustrated by the following non-limiting Examples.

EXAMPLES

Example 1—Identification of Naltrexone as an Antagonist of TLR9

Low dose naltrexone (LDN) was tested in agonist and antagonist assays on a panel of TLR and NOD transfectants (TLR2, TLR3, TLR4, TLR5, TLR7, TLR8, TLR9, NOD1, NOD2). Screening assays were performed by Cayla-Invivogen (Toulouse, France). In agonist assays, LDN did not stimulate signalling through any of the receptors tested. In antagonist assays, the mild antagonist effect observed by Hutchinson et al. (2008) for TLR4 was replicated, but a more striking effect was seen for TLR9, for which LDN inhibited recognition of CpG DNA (FIG. 1). A subsequent titration suggested an IC50 of approximately 50 µM (FIG. 2).

Example 2—LDN in the Treatment of Melanoma

Patient with chemotherapy-resistant metastatic melanoma showed a marked clinical response to LDN in combination with vitamin D3, which was maintained for nine months.

The patient had a recurrent head and neck melanoma and had previously been treated with a vaccine and radiotherapy, but had failed to respond to this and had developed a new metastatic disease in the chest.

Low dose naltrexone was administered as a supportive treatment prior to more radiotherapy. Within 48 hours the patient developed marked vitiligo which is a sign of activated effective cytotoxic T cells against the antigens associated with melanoma. It was concluded that the naltrexone had activated the vaccine. The patient responded to radiotherapy to the chest lesions.

Example 3—LDN in the Treatment of Prostate Cancer

Patient with hormone-refractory prostate cancer and marked lymphadenopathy being treated with *Mycobacterium vaccae* (a TLR2-stimulating vaccine) showed a marked response with the addition of LDN, including a drop in prostate-specific antigen levels.

REFERENCES

Boasso, A., C. M. Royle, S. Doumazos, V. N. Aquino, M. Biasin, L. Piacentini, B. Tavano, D. Fuchs, F. Mazzotta, and S. L. Caputo. 2011. Overactivation of plasmacytoid dendritic cells inhibits antiviral T-cell responses: a model for HIV immunopathogenesis. *Blood* 118:5152-5162.

Berkson, B. M., D. M. Rubin, and A. J. Berkson. 2006. The long-term survival of a patient with pancreatic cancer with metastases to the liver after treatment with the intravenous alpha-lipoic acid/low-dose naltrexone protocol. *Integr Cancer Ther* 5:83-89.

Berkson, B. M., D. M. Rubin, and A. J. Berkson. 2009. Revisiting the ALA/N (alpha-lipoic acid/low-dose naltrexone) protocol for people with metastatic and nonmetastatic pancreatic cancer: a report of 3 new cases. *Integr Cancer Ther* 8:416-422.

Donahue, R. N., P. J. McLaughlin, and I. S. Zagon. 2011a. Low-dose naltrexone suppresses ovarian cancer and exhibits enhanced inhibition in combination with cisplatin. *Experimental Biology and Medicine* 236:883-895

Donahue, R. N., P. J. McLaughlin, and I. S. Zagon. 2011b. Low-dose naltrexone targets the opioid growth factor-opioid growth factor receptor pathway to inhibit cell proliferation: mechanistic evidence from a tissue culture model. *Experimental Biology and Medicine* 236:1036-1050.

Hutchinson, M. R., Y. Zhang, K. Brown, B. D. Coats, M. Shridhar, P. W. Sholar, S. J. Patel, N. Y. Crysdale, J. A. Harrison, S. F. Maier, K. C. Rice, and L. R. Watkins. 2008. Non-stereoselective reversal of neuropathic pain by naloxone and naltrexone: involvement of toll-like receptor 4 (TLR4). *Eur J Neurosci* 28:20-29.

Hytrek, S. D., P. J. McLaughlin, C. M. Lang, and I. S. Zagon. 1996. Inhibition of human colon cancer by intermittent opioid receptor blockade with naltrexone. *Cancer letters* 101:159-164.

Mantovani, A. 2008. Cancer: inflaming metastasis. *Nature* 457:36-37.

Rahn, K. A., P. J. McLaughlin, and I. S. Zagon. 2011. Prevention and diminished expression of experimental autoimmune encephalomyelitis by low dose naltrexone (LDN) or opioid growth factor (OGF) for an extended period: therapeutic implications for multiple sclerosis. *Brain research*.

Smith, J. P., S. I. Bingaman, F. Ruggiero, D. T. Mauger, A. Mukherjee, C. O. McGovern, and I. S. Zagon. 2011. Therapy with the opioid antagonist naltrexone promotes mucosal healing in active Crohn's disease: a randomized placebo-controlled trial. *Dig Dis Sci* 56:2088-2097.

Takagi, H., T. Fukaya, K. Eizumi, Y. Sato, K. Sato, A. Shibazaki, H. Otsuka, A. Hijikata, T. Watanabe, and O. Ohara. 2011. Plasmacytoid Dendritic Cells Are Crucial for the Initiation of Inflammation and T Cell Immunity In Vivo. *Immunity* 35:958-971.

Weber, C., C. Mailer, A. Podszuweit, C. Montino, J. Vollmer, and A. Forsbach. 2012. TLR3 immune modulation by unformulated siRNA or DNA and the role of CD14 (in TLR mediated effects). *Immunology*.

Wingender, G., N. Garbi, B. Schumak, F. Jangerkes, E. Endl, D. von Bubnoff, J. Steitz, J. Striegler, G. Moldenhauer, and T. TÃting. 2006. Systemic application of CpG-rich DNA suppresses adaptive T cell immunity via induction of IDO. *European journal of immunology* 36:12-20.

Zagon, I. S., and P. J. McLaughlin. 1983. Naltrexone modulates tumour response in mice with neuroblastoma. *Science* 221:671.

The invention claimed is:

1. A method of treating metastatic melanoma, comprising administering to a subject in need thereof naltrexone, or a pharmaceutically acceptable salt thereof, in combination with Vitamin D3.

2. The method according to claim 1, wherein the naltrexone, or the pharmaceutically acceptable salt thereof, is administered at a dose of between 0.01 mg/kg and 0.08 mg/kg.

3. The method of claim 2, wherein the dose is between 0.03 mg/kg and 0.06 mg/kg.

4. The method of claim 2, wherein the dose is between 0.04 mg/kg and 0.05 mg/kg.

* * * * *